Oct. 11, 1966 G. MERRILL Plant Pat. 2,676
PEACH TREE
Filed May 17, 1965
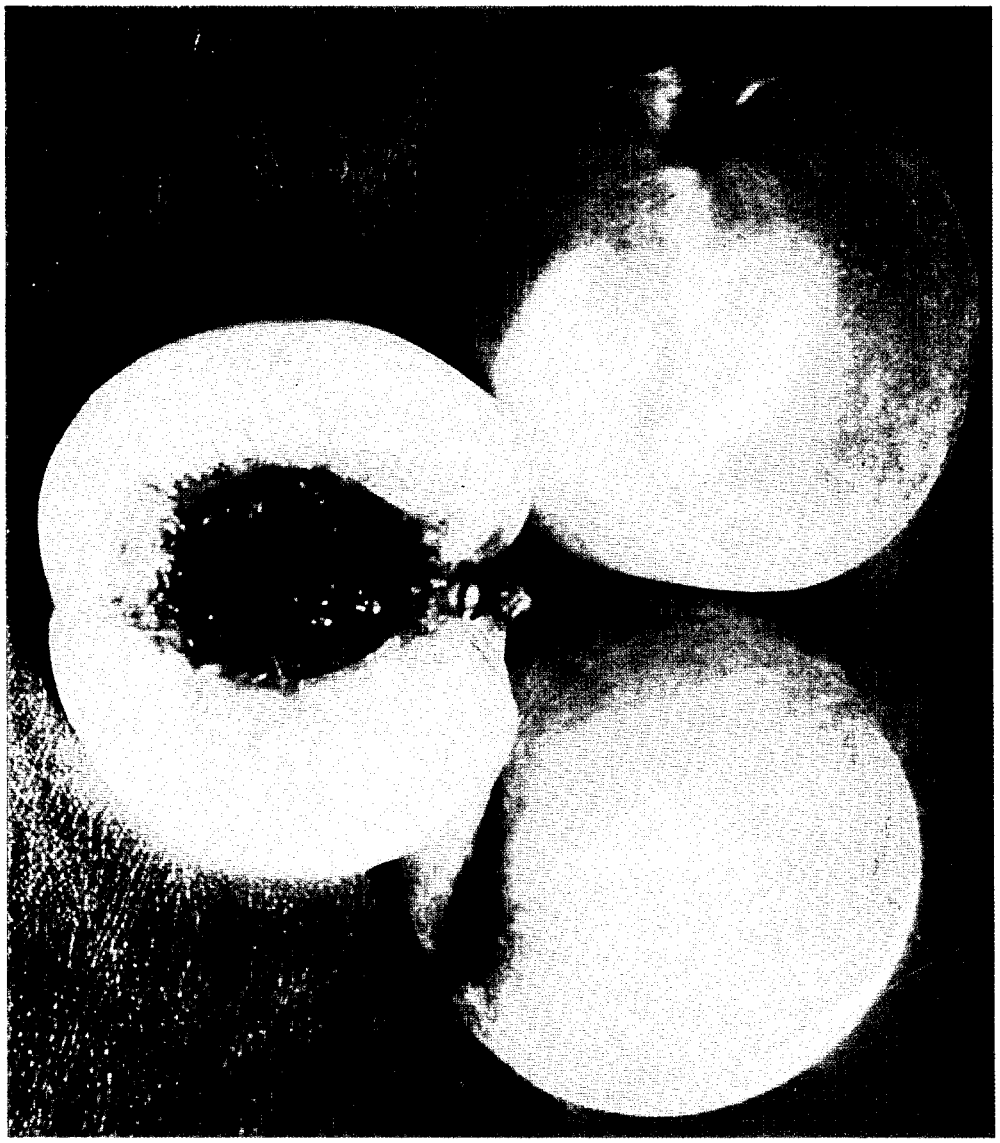
GRANT MERRILL
INVENTOR
Hubbell & Worrel
ATTORNEYS United States Patent Office Plant Pat. 2,676
Patented Oct. 11, 1966

2,676
PEACH TREE

Grant Merrill, 416 N. Anderson Road, Exeter, Calif.

Filed May 17, 1965, Ser. No. 456,585
1 Claim. (Cl. Plt.—43)

The present invention relates to a peach tree and more particularly to a new and distinct variety thereof broadly characterized by its large size; vigorous and regular bearing; early bloom; and the production of highly colored, yellow, red-striped skin, freestone, firmly textured, yellow-fleshed peaches.

The instant variety peach tree blooms at a time which is generally regarded as somewhat early, being about the same time as the July Elberta of U.S. Plant Patent No. 15. Its fruit ripens two to three weeks earlier than that of the Carnival peach tree of U.S. Plant Patent No. 2,144, which the instant variety most closely resembles. Its fruit is distinguished therefrom, however, by being somewhat smaller in size and providing a more attractive yellow, red-striped skin color. The flesh of the fruit of the instant variety is further distinguished from that of the Carnival in its firmer texture adjacent to the skin which retains such firmness for a longer period when left on the tree after ripe so that the tree can be harvested in one picking.

I originated the present variety of peach tree on a farm formerly owned by me near Red Bluff, Tehama County, California. I first crossed a J. H. Hale peach tree (unpatented) with an open pollinated seedling of a cross between a Maxine peach tree (unpatented) and a July Elberta peach tree of U.S. Plant Patent No. 15. This cross was propagated and produced a number of different varieties from which I selected the instant variety as the most desirable for commercial production. Buds from the new selected tree were budded into a number of Nemaguard seeding peach trees (unpatented) at a nursery at Le Grand, Merced County, California, in May 1962. The budded plants of the instant variety were planted in a test plot at Dinuba, Tulare County, California, in 1963. The trees fruited in July 1964 and the fruit and tree characteristics resulting from such budding proved identical to those of the original tree.

The accompanying drawing is a dye transfer color print of a photograph of three mature fruit of the subject variety with one divided on its suture plane to reveal flesh coloration and pit characteristics.

Referring more specifically to the pomological details of this new and distinct variety of peach tree, the following has been observed under the ecological conditions prevailing at the test plot at Dinuba, Tulare County, California, and is an outlined description thereof. All major color plate identifications are by reference to the Nickerson Color Fan of the American Horticultural Council.

*Tree*

Size: Large, vigorous, generally upright, with shape and density determined by pruning methods.
Trunk: Medium stocky, medium shaggy.
Branches: Lenticels, numerous, medium sized.
Leaves: (Selected from midportion of vigorous unbranched terminal shoots 18" to 24" long.)
*Size.*—Large.
*Length.*—7" to 8½", average 7¾".
*Width.*—1⅛" to 1⅜", average 1¼".
*Form.*—Lanceolate, tip acuminate, long, medium thick.
*Color.*—Upper surface, medium green with a lighter green under-surface; midrib, under-surface, yellowish-green.

*Class.*—(Meader & Blake: Proceedings of Am. Soc. Hor. Sc., vol. 37, page 206).—1, 2 and 3.
*Margin.*—Glandular, crenate.
*Petiole.*—Medium long, medium slender.
*Stipules.*—At base of leaf, falling off early.
*Glands.*—Varying in number from two to eight, mostly on petiole and base of leaves, reniform.
Flower Buds: Medium size, plump, free, pubescent.
Flowers: Generally early, small size, salmon pink color. Pollen—abundant.

*Fruit*

Maturity when described: Firm ripe.
Size: Medium.
*Axial diameter.*—2½" to 2¾", average 2⅝", under normal environmental and horticultural conditions with usual thinning to space fruit 6" to 8" on fruit-bearing branches.
*Transverse in suture plane.*—2⅝" to 3⅛", average 2⅞".
*At right angle to suture plane.*—2⅝" to 2⅞", average 2¾".
Form: Usually uniform, generally globose, frequently flattened toward base on one side.
*Suture.*—Inconspicuous, shallow, with slight depression beyond pistil point.
*Ventral surface.*—Rounded, slightly lipped, lips unequal.
*Cavity.*—Abrupt, deep, ellongated in suture plane, with suture showing on both sides. Depth—average ½". Breadth—average ¾".
*Base.*—Retuse.
*Apex.*—Usually depressed, small tip below depressed area.
*Pistil point.*—Small, apical.
*Stem.*—Length, ¼" to ½", average ⅜". Diameter—average ⅛".
Skin: Medium thick, medium tough.
*Under color.*—Strong yellow (5Y 7/10) with varying amounts of dark reddish-orange (10R 4/9) blush in stripes covering from approximately 50% to 80% of the surface.
*Down.*—Scant, short, does not usually roll up when rubbed.
Flesh:
*Color.*—Brilliant yellow (2.5Y 9/9) to vivid yellow (2.5Y 8/12), some dark reddish-orange (7.5R 4/11) near pit.
*Amygdalin.*—Moderate.
*Juice.*—Moderate.
*Texture.*—Generally firm, with greater firmness near the skin.
*Fibers.*—Few, fine and tender.
*Ripens.*—Evenly, softening first adjacent to the stone while remaining firm adjacent to the skin.
*Flavor.*—Mild, delicate.
*Aroma.*—Distinct.
*Eating quality.*—Good.
Stone: Generally free from the flesh, sometimes adheres to the flesh on less mature fruit along the ventral edge near the base.
*Fibers.*—Short.
*Size.*—Length, 1¼" to 1¾", average 1½". Breadth, ⅞" to 1⅛", average 1".
*Form.*—Generally obovate, tip acuminate.
*Base.*—Straight to slightly oblique.
*Hilum.*—Oval.
*Tip.*—Acuminate.
*Sides.*—Usually equal.
*Surface.*—Irregularly furrowed toward apex along the ventral and dorsal edges, pitted toward base.
*Ridges.*—Jagged.

*Pits.*—Generally circular, some oval.

*Ventral edge.*—Thick, with some ridges.

*Dorsal edge.*—Narrow, usually two distinct ridges, broken at intervals.

*Color.*—Brown, with some red at the base and apex.

Use: Fresh market, local and distinct, culinary.

*Keeping quality.*—Good.

*Shipping quality.*—Good.

Although the new variety of peach tree possesses the described characteristics as a result of the growing conditions in Tehama County, California, having first been observed near Red Bluff, Tehama County, California at the northern end of the Sacramento Valley, and later confirmed at Dinuba in Tulare County, California in the central portion of the San Joaquin Valley, it is to be understood that variation of the usual magnitude in characteristics incident to the growing conditions, fertilization, pruning and pest control are to be expected.

Having thus described and illustrated my new variety of peach tree, what is claimed as new and desired to be secured by Letters Patent is:

A new and distinct variety of peach tree substantially as illustrated and described and which is characterized by its large vigorous growth; its early blooming, about the same time as the July Elberta of U.S. Plant Patent No. 15; and its regular and heavy bearing of freestone, yellow-fleshed peaches which ripen two to three weeks earlier than the fruit of the Carnival peach tree of U.S. Plant Patent No. 2,144, which it most nearly resembles but from which it is distinguished in its somewhat smaller fruit having a more highly colored yellow red-striped skin with flesh that is firmer near the skin when ripe and which retains such firmness for a longer period on the tree so that the fruit can be harvested in one picking.

No references cited.

ABRAHAM G. STONE, *Primary Examiner.*

R. E. BAGWILL, *Assistant Examiner.*